(12) United States Patent
Popov et al.

(10) Patent No.: US 9,772,298 B2
(45) Date of Patent: Sep. 26, 2017

(54) METHOD AND APPARATUS FOR DETERMINING THERMAL CONDUCTIVITY AND THERMAL DIFFUSIVITY OF A HETEROGENEOUS MATERIAL

(71) Applicant: SCHLUMBERGER TECHNOLOGY CORPORATION, Sugar Land, TX (US)

(72) Inventors: Yury Popov, Moscow (RU); Evgeny Popov, Moscow (RU); Anton Parshin, Ufa (RU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 408 days.

(21) Appl. No.: 14/465,972

(22) Filed: Aug. 22, 2014

(65) Prior Publication Data

US 2015/0055676 A1 Feb. 26, 2015

(30) Foreign Application Priority Data

Aug. 23, 2013 (RU) .................................. 2013139145

(51) Int. Cl.
*G01N 25/18* (2006.01)
*G01N 33/24* (2006.01)

(52) U.S. Cl.
CPC ............. *G01N 25/18* (2013.01); *G01N 33/24* (2013.01)

(58) Field of Classification Search
None
See application file for complete search history.

(56) References Cited

U.S. PATENT DOCUMENTS

2006/0222043 A1* 10/2006 Cahill .................... G01N 25/18
374/44
2013/0316519 A1* 11/2013 Mitzi ................. H01L 21/02422
438/478
2014/0294039 A1* 10/2014 Popov .................... G01N 25/18
374/44

OTHER PUBLICATIONS

Popov et al., "Complex Detailed Investigations of the Thermal Properties of Rocks on the Basis of a Moving Point Source," Izvestiya, Earth Physics, 1985, vol. 21(1): pp. 64-70.
Popov et al., "SGP-TR-194: New Methods and Instruments for Determination of Reservoir Thermal Properties," Thirty-Seventh Workshop on Geothermal Reservoir Engineering, Jan.-Feb. 2012: pp. 1-11.

* cited by examiner

*Primary Examiner* — Erica Lin

(57) ABSTRACT

Surface of a sample of a heterogeneous material and of samples with known thermal conductivity and thermal diffusivity is heated by a heating spot created by a heater and moving along the surfaces of all samples to determine thermal conductivity and thermal diffusivity of the heterogeneous material. Temperatures of heated surface of all samples are registered by three temperature sensors. Return of the heater and the sensors to the initial position is used for scanning with additional measurements of the sample thermal conductivity for a layer of the sample with depth and width different from those of a layer where thermal conductivity is measured during the forward direction.

5 Claims, 1 Drawing Sheet

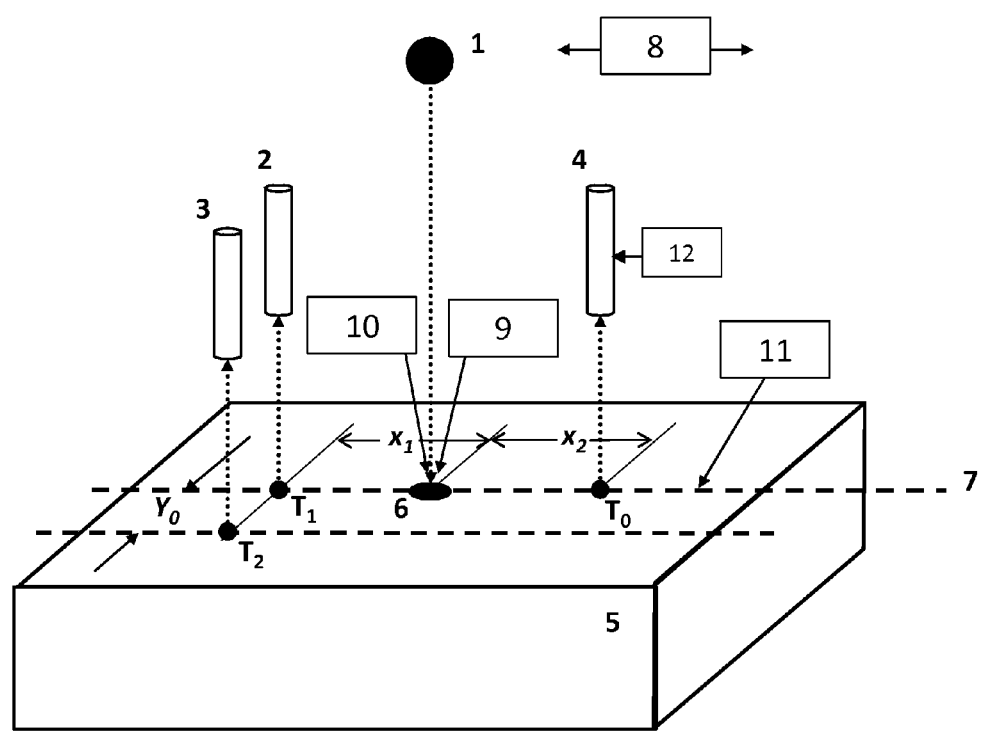

METHOD AND APPARATUS FOR DETERMINING THERMAL CONDUCTIVITY AND THERMAL DIFFUSIVITY OF A HETEROGENEOUS MATERIAL

CROSS-REFERENCE TO RELATED APPLICATION

This application claims priority to Russian Patent Application No. 2013139145 filed Aug. 23, 2013, which is incorporated herein by reference in its entirety.

BACKGROUND

The disclosure relates to studying physical properties of heterogeneous materials and can be used for analyzing texture, structure, porosity, thermal conductivity, thermal diffusivity, and volumetric heat capacity of geomaterials, constructional and other natural and industrial materials in different science and technology areas.

There is a known method and apparatus fir determining thermal conductivity and thermal diffusivity described in article "New methods and instruments for determination of reservoir thermal properties," by Popov, Yu., Bayuk, I., Parshin, A., Miklashevskiy, D., Novikov, S., Chekhonin, E. and Proceedings, Thirty-Seventh Workshop on Geothermal Reservoir Engineering, Stanford University, Stanford, Calif., Jan. 30-Feb. 1, 2012, SGP-TR-194. In the known apparatus, a first sensor records a temperature of a heated surface of a sample of a heterogeneous material and of samples with known thermal conductivity and thermal diffusivity along a heating line at a distance $X_1$ from a moving heating spot created by a heater. A second temperature sensor is installed at the same distance $X_1$ from the heating spot, along the heating line, and at a distance $Y_o$ from the heating line and records surface temperatures of the sample of the heterogeneous material and of the samples with known thermal conductivity and thermal diffusivity along a line parallel to the heat spot trajectory and located at the distance $Y_o$ from it. A third sensor records an initial temperature of the sample of the heterogeneous material and the samples with known thermal conductivity and thermal diffusivity along the heating line and is installed along the heating spot trajectory, in front of the heating spot, at an arbitrary distance $X_2$ from it.

These known method and apparatus has such disadvantages as a need to return a unit with the heater and the temperature sensors to the initial position for the next measurement; in this process, when the unit with the heater and the temperature sensors are returned to the initial position, no measurements are carried out, which results in nonproductive time. Besides, within a single measurement cycle including scanning of the samples in a forward direction and return of the unit with the heater and the temperature sensors to the initial position, it is not possible to measure thermal conductivity for sample layers with different thickness and width, i.e. it is impossible to determine thermal conductivity for layers with different thickness and width in a heterogeneous sample, which is important for describing heterogeneity of the samples. It is also impossible to obtain high-detail profiles of thermal conductivity distribution along the scanning line with a high spatial resolution. This is due to the fact that such high-detail measurements require maximal decrease of the distance $X_1$ between the sensors measuring sample surface heating temperature and the heating spot, which results in unacceptable decrease in a thickness of a layer of the heterogeneous sample and appropriate decrease in a volume of the heterogeneous sample. Besides, significant decrease in the distance $X_1$ results in a loss of accuracy of thermal conductivity and thermal diffusivity measurements because the actual heating spot cannot be considered as a point heating source taken as a basis for a theoretical model of measuring thermal conductivity and thermal diffusivity by this method. Then, in case of significant decrease in the distance $X_1$, heating temperature within an area of its registration by the second sensor becomes so low that the second sensor will record it with inadmissible signal-to-noise ratio, which will result in loss of opportunity for high quality measurements of thermal diffusivity. Besides, a maximal decrease in the distance $X_1$ results in significant decrease in temperature registered by the second temperature sensor, which results in an extremely low accuracy of thermal diffusivity measurements and, as a consequence, to a loss of opportunity for high-quality measurements of thermal diffusivity. One more disadvantage of the known method is that thermal conductivity and thermal diffusivity measurements and registration of heterogeneity of the heterogeneous material sample are carried out only along one scanning line, which restricts information on a degree, nature, and spatial distribution of material heterogeneity and quality of data on its thermal conductivity and thermal diffusivity.

SUMMARY

The disclosure provides for determining thermal conductivity and thermal diffusivity of heterogeneous materials with measurement layers of different depth and width and for simultaneous registration of heterogeneity distribution in samples of heterogeneous materials with a high spatial resolution, as well as for measuring thermal conductivity and registering heterogeneity distribution along an additional scanning line.

In accordance with the proposed method for determining thermal conductivity and thermal diffusivity of a heterogeneous material, a surface of a sample of the heterogeneous material and samples with the known thermal conductivity and thermal diffusivity are heated by a heating spot created by a heater with an initial power, moving along the surface of the sample of the heterogeneous material in a straight line with a constant initial velocity. Temperatures of the heated surface of the sample of the heterogeneous material and of the surfaces of the samples with the known thermal conductivity and thermal diffusivity are registered at a first distance behind the moving heating spot along a trajectory of the heating spot by means of a first temperature sensor moving along the trajectory of the heating spot with a velocity equal to the initial velocity of the heating spot. Temperatures of the surface of the sample of the heterogeneous material and of the surfaces of the samples with the known thermal conductivity and thermal diffusivity are registered along a line parallel to the trajectory of the heating spot and located at a second distance from the trajectory of the heating spot by means of a second temperature sensor moving along the line parallel to the trajectory of the heating spot with a velocity equal to the initial velocity of the heating spot. Initial temperatures of the surface of the sample of the heterogeneous material and of the samples with the known thermal conductivity and thermal diffusivity are registered in front of the heating spot by means of a third temperature sensor moving along the trajectory of the heating spot with a velocity equal to the initial velocity of the heating spot. After completion of registration of the surface temperatures of the sample of the heterogeneous material and of the samples with the known thermal conductivity and thermal diffusivity, ensuring measurements for a layer of the sample of the heterogeneous material with initial depth and width, moving direction of the heating spot and of the temperature sensors relative to the sample of the heterogeneous material and to the samples with the known thermal conductivity and thermal diffusivity is changed to opposite. The surface of the sample of the heterogeneous material is heated by the heating spot with a dimension different from the initial dimension and created by the heater with a capacity different from the initial power moving along the surface of the sample of the heterogeneous material and the surfaces of the samples with the known thermal conductivity and thermal diffusivity in a straight line in the opposite direction with a constant velocity different from the initial velocity and preventing overheating and/or destruction of the sample of the heterogeneous material. The third sensor moving along the trajectory of the heating spot in the opposite direction with a velocity equal to the velocity of the heating spot registers a temperature of the heated surface of the sample of the heterogeneous material; a distance between the third temperature sensor and the heating provides measurements for a layer of the sample of the heterogeneous material with depth and width different from the initial depth and width. The first temperature sensor moving along the trajectory of the heating spot in the opposite direction with a velocity equal to the velocity of the heating registers initial temperatures of the surface of the sample of the heterogeneous material and of the samples with the known thermal conductivity and thermal diffusivity, at the first distance in front of the heating spot along the trajectory of the heating spot. After completion of measurements, based on results of temperatures registration by the temperature sensors in the forward and opposite directions and data on thermal conductivity and thermal diffusivity of the samples with the known thermal conductivity and thermal diffusivity, a distribution of thermal conductivity and thermal diffusivity is determined for the sample of the heterogeneous material along the trajectory of the heating spot in the layers of the sample with different depth and width.

The distance between the third temperature sensor and the heating spot can be selected to simultaneously ensure a required accuracy of the measurements and a highest spatial resolution when registering the sample heterogeneity along the line of thermal conductivity profile measurements.

The distance between the third temperature sensor and the heating spot can be set in advance, before heating and measurements, or before heating and measurements carried out during moving in the opposite direction.

Heating of the surface of the sample of the heterogeneous material by the heating spot moving along the surface of the sample in a straight line in the opposite direction can be carried out along the line parallel to the initial heating line.

An apparatus for determining thermal conductivity and thermal diffusivity of a heterogeneous material a movable heater to create a heating spot on a surface of a sample of the heterogeneous material and on surfaces of samples with known thermal conductivity and thermal diffusivity and first, second, and third temperature sensors. The first and the third sensors are located on opposite sides of the heater to register temperatures of the surface of the sample of the heterogeneous material sample and of the samples with the known thermal conductivity and thermal diffusivity along a trajectory of the heating spot at different distances from the heating spot. The second sensor is provided to register temperatures of the surface of the sample of the heterogeneous material and of the samples with the known thermal conductivity and thermal diffusivity along a line parallel to a trajectory of the heating spot. The apparatus also comprises a unit to change dimensions of the heating spot, a unit to change a velocity of the heating spot, a unit to change a power of the heater, a unit to adjust a distance between the third temperature sensor and the heating spot, and a unit to displace the trajectory of the heating spot.

A laser can be used as the heater. Additionally, the apparatus can comprise a unit to focus the laser emission to provide required shape and dimensions of the heating spot.

An electric lamp can be used as the heater. In this case, it can be required to include into the apparatus a unit to focus the electric lamp emission in order to provide required shape and dimensions of the heating spot.

According another embodiment of the disclosure an electric lamp with a built-in block to focus the electric lamp emission can be used as the heater in order to provide required shape and size of the heating spot.

In accordance with another embodiment a hot gas stream coming out from a nozzle providing required shape and dimensions of the heating can be used as the heater.

BRIEF DESCRIPTION OF DRAWING

The disclosure is illustrated by a drawing where FIG. 1 shows a scheme of one embodiment of the proposed apparatus.

DETAILED DESCRIPTION

Proposed method and apparatus provide determining of thermal conductivity and thermal diffusivity of heterogeneous materials with different measurement depths and registration of heterogeneity of heterogeneous materials (rocks, etc.) with a high spatial resolution capacity.

As shown on FIG. 1, an apparatus for determining thermal conductivity and thermal diffusivity comprises a heater 1, a first sensor 2, a second sensor 3 and a third sensor 4 for registering surface temperature of a sample 5 of a heterogeneous material. The apparatus also comprises a unit 8 to change moving velocities of the heater 1 and the sensors 2, 3, and 4; a unit 9 to change a power of the heater; a unit 10 to change dimensions of a heating spot 6; and a unit 11 to displace a trajectory of the heating spot (a heating line) to a predetermined value when moving in an opposite direction.

A surface of the sample 5 of the heterogeneous material 5 and samples with known thermal conductivity and thermal diffusivity (not shown on the drawing) are heated by the heating spot 6 having an initial dimension and created by the heater 1 with an initial power moving along the surface of the sample 5 in an initial straight line 7 with an initial constant moving velocity.

The first sensor 2 registers temperature $T_1$ of the heated surface of the sample 5 of the heterogeneous material and of the samples with the known thermal conductivity and thermal diffusivity at a first distance $X_1$ from the moving heating spot 6 created by the heater 1. The second sensor 3 is disposed at the same distance $X_1$ from the heating spot 6, along an initial heating line 7 and registers surface temperature $T_2$ of the sample 5 of the heterogeneous material and of the samples with the known thermal conductivity and thermal diffusivity along a line parallel to a trajectory of the heating spot 6 and disposed at a distance $Y_o$ from it. The third sensor 4 registers initial temperature $T_0$ of the sample 5 along the heating line 7 and is installed in front of the heating spot 6 on the heating spot 6 trajectory at the second distance $X_2$ from the heating spot.

According to an embodiment of the disclosure, a return of the heater and of the temperature sensors to the initial position is used for scanning in opposite direction with additional measurements of the sample thermal conductivity and registration of the sample heterogeneity. A distance between the third temperature sensor and the heating spot is set so as to provide, together with velocity, power and dimensions of the heating spot, a required depth and width of the layer where thermal conductivity is measured during moving in the opposite direction, these depth and width are different from those of the layer where thermal conductivity is measured during moving in the forward direction. In this case, during scanning in the opposite direction, initial temperatures along the trajectory of the heating spot 6 are determined by the first sensor 2; and the third sensor 4 is used to register a heating temperature for measuring thermal conductivity. The required distance between the third sensor 4 and the heating spot 6 can be set after moving of the heating spot in the forward direction is completed or before it begins. Since the first sensor 2 and the third sensor 4 are disposed at different distances from the heating spot 6 and movement in forward and backward directions is with different velocities, this ensures different depth and width of a measurement layer for the sample 5 during forward and backward direction.

Before scanning in the opposite direction, moving velocities of the heater 1 and of the sensors 2, 3, and 4 are changed to a predetermined value by means of the unit 8, dimensions of the heating spot 6 are changed to a predetermined value by means of the unit 10, useful power of the heater 1 in the heating spot is changed by means of the unit 9, setting their values so that, while measuring thermal conductivity during scanning in the opposite direction, to simultaneously ensure a required accuracy of thermal conductivity measurements, to prevent overheating and/or destruction of the sample 5, and to ensure that depths and widths of layers where thermal conductivity is measured are different from those measured during the forward scanning. The apparatus comprises the unit 12 to adjust distances between the third temperature sensor and the heating spot so that to simultaneously ensure the highest of spatial resolution capacity when registering the sample heterogeneity for the thermal conductivity profile and that depths and widths of layers where thermal conductivity is measured are different from those measured during the forward scanning.

A laser can be used as the heater 1. Additionally, the apparatus can comprise a unit to focus the laser emission to provide required shape and dimensions of the heating spot.

An electric lamp can also be used as the heater 1. In this case, it can be required to include into the apparatus a unit to focus the electric lamp emission in order to provide required shape and dimensions of the heating spot.

According another embodiment of the disclosure the heater 1 can be an electric lamp with a built-in block to focus the electric lamp emission in order to provide required shape and dimensions of the heating spot.

According another embodiment of the disclosure a hot gas stream coming out from a nozzle providing required shape and dimensions of the heating spot can be used as the heater 1.

As an example, thermal conductivity and thermal diffusivity of a heterogeneous rock sample, namely, sandstone 100 mm long, 80 mm wide and 40 mm thick, were determined. The following samples are used as the samples with the known thermal conductivity and thermal diffusivity: a sample of industrial glass KV with thermal conductivity of 1.35 W/(m·K) and thermal diffusivity of $0.83 \cdot 10^{-6}$ m²/s, 70 mm long, 60 mm wide, and 40 mm thick, and a sample of white marble with thermal conductivity of 3.15 W/(m·K) and и thermal diffusivity of $1.42 \cdot 10^{-6}$ m²/s, 70 mm long, 60 mm wide, and 40 mm thick. Continuous wave laser ILGN-703 is used as the heater 1, with variable useful power from 0.05 to 10 W in the heating spot and a variable diameter of the heating spot ranging within 1-8 mm. Three infrared radiometers of Kelvin type with a vision field of 1.5×1.5 mm are used as non-contact temperature sensors 2, 3, and 4. A thin black enamel coat 20-30 μm thick is applied to the largest surfaces of sandstone, industrial glass, and marble samples to add to these surfaces similar optical properties (absorption and radiation factors), which is required for similar heat capacity of all samples and similar accuracy of temperature registration based on infrared radiation of surfaces for all samples. The sandstone sample together with the industrial glass and white marble samples are installed sequentially in a line on a movable platform for their subsequent heating by the moving heating spot. Distance $X_1=30$ mm is set between the heating spot and each vision field of the sensors 2 and 3 along the heating line, distance $Y_0=6$ mm is set between the field vision of the sensor 3 and the heating line, the heating spot diameter is set to 4 mm, and the laser power is set to ensure a useful power of 1.5 W in the heat spot. Distance $X_2$ between the vision field of the sensor 4 and the heating spot along the heating line is set to 5 mm, but it must be sufficient so that laser emission reflected from the sample surfaces does not get the vision field of the sensor 4, which results in severe distortion of temperature measurement results, and at the same time it must be minimal to ensure maximum possible spatial resolution to register sandstone sample heterogeneity when the platform and the heated samples moves in the opposite direction. The distance $X_2=5$ mm will also ensure the much less depth and width of the layer where thermal conductivity is measured during the platform moving in the opposite direction as compared to its forward moving. Then the platform is set to motion with all samples in front of the laser and the sensors so that the heating spot and sensor vision fields move with a constant velocity of 3 mm/s, sequentially, in relation to all samples. During the movement, sample surfaces are heated with the constant useful power of 1.5 W in the heating spot. During the heating, the temperature sensor 4 registers initial temperatures of the samples in front of the heating spot and the temperature sensors 2 and 3 register the heating temperature along the heating line and parallel line behind the heating spot. After completion of the samples heating and registration of their initial temperatures, heating temperatures and, as a result, excess heating temperatures by means of known relationships mentioned in article "New methods and instruments for determination of reservoir thermal properties" by Popov, Yu., Bayuk, I., Parshin, A., Miklashevskiy, D., Novikov, S., Chekhonin, E. and Proceedings, Thirty-Seventh Workshop on Geothermal Reservoir Engineering, Stanford University, Stanford, Calif., Jan. 30-Feb. 1, 2012, SGP-TR-194, based on heating temperatures registered by the sensors 2, 3, and 4 and known thermal conductivity and thermal diffusivity values of two samples placed sequentially with the sandstone sample, values of sandstone thermal conductivity and thermal diffusivity are determined in the points of the line along the sandstone sample, which appear varying within a range of 1.4 . . . 3.1 W/(m·K) for thermal conductivity and (0.9 . . . 1.5)·$10^{-6}$ m²/s for thermal diffusivity due to heterogeneity of the sandstone sample. The unit 8 is used to increase opposite moving velocity of the platform to 8 mm/s for additional significant (several times) decrease in the depth and width of the measurement layer during the platform moving in the opposite direction. Then, the unit 11 is used to place the sandstone sample on the platform so that a future heating line, during the moving in the opposite direction, is displaced by 10 mm in parallel to the heating line during the forward moving, to ensure evaluation of the sandstone sample heterogeneity along the new trajectory of the heating spot. To retain accuracy of thermal conductivity and thermal diffusivity measurements, the unit 10 is used to reduce the heating spot diameter to 1 mm and the unit 9 is used to reduce the laser power to 0.2 W to prevent overheating of the samples in the heating spot due to increased energy concentration in the heating spot. Then the platform is moved in the opposite direction with all samples in front of the laser and the sensors; the platform will move with a specified velocity of 8 mm/s in relation to the heating spot and sensor vision fields; in this case the heating line will move along the sandstone sample, 10 mm away from the heating line during the platform forward moving. During the heating in the opposite direction, the temperature sensor 2 registers initial temperatures of the samples in front of the heating spot and the temperature sensor 4 registers the heating temperature along the heating line. After completion of the samples heating and registration of their heating temperatures while the platform moves in the opposite direction, by means of the same known relationships on excess temperatures registered by the sensors 2 and 4 and the known thermal conductivity and thermal diffusivity values of two samples placed sequentially with the sandstone sample, values of sandstone thermal conductivity are determined in the points of the heating spot trajectory along the sandstone sample, and these values are already in a different range of 1.8 . . . 2.5 W/(m·K) for the heating line during the moving in the opposite direction, which makes it possible to conclude that the sandstone sample is heterogeneous not just along the heating line during the forward moving, but also in other directions on the sandstone sample.

The distance $X_2$ between the sensor 4 and the heating spot in front of the heating spot and the sensors moving in forward direction in relation to the sample and the samples with the known thermal conductivity and thermal diffusivity can be set equal to 30 mm; after moving in the forward direction is completed, this distance $X_2$ is set to 5 mm to ensure new thickness and width of the layer of the heterogeneous material sample and the highest spatial resolution while registering the sample heterogeneity during scanning in the opposite direction. Then, the heating spot and the temperature sensors are set to motion in the opposite direction in relation to the heterogeneous material sample and the samples with known thermal conductivity and thermal diffusivity.

The invention claimed is:

1. A method for determining thermal conductivity and thermal diffusivity of a heterogeneous material comprising:
heating a surface of a sample of the heterogeneous material and samples with known thermal conductivity and thermal diffusivity by a heating spot having an initial dimension and created by a heater with an initial power, the heating spot moving along the surface of the sample of the heterogeneous material and the samples with the known thermal conductivity and thermal diffusivity along a straight line with a constant initial velocity,
registering a temperature of the heated surface of the sample of the heterogeneous material and of the heated samples with the known thermal conductivity and thermal diffusivity at a first distance behind the moving heating spot along a trajectory of the heating spot by a first temperature sensor moving along the trajectory of the heating spot with a velocity equal to the initial velocity of the heating spot,
registering a temperature of the surface of the sample of the heterogeneous material and of the samples with the known thermal conductivity and thermal diffusivity along a line parallel to the trajectory of the heating spot and located at a second distance from the trajectory of the heating spot by a second temperature sensor moving along the line parallel to the trajectory of the heating spot with a velocity equal to the initial velocity of the heating spot,
registering initial temperatures of the surface of the sample of the heterogeneous material and of the samples with the known thermal conductivity and thermal diffusivity in front of the heating spot along the trajectory of the heating spot by a third temperature sensor moving along the trajectory of the heating spot with a velocity equal to the initial velocity of the heating spot,
changing direction of the heating spot and the temperature sensors moving relative to the sample of the heterogeneous material and the samples with the known thermal conductivity and thermal diffusivity to an opposite direction after completion of registration of the surface temperature of the sample of the heterogeneous material and of the samples with the known thermal conductivity and thermal diffusivity ensuring measurements for a layer of the sample of the heterogeneous material with initial depth and width,
heating the surface of the sample of the heterogeneous material and the samples with the known thermal conductivity and thermal diffusivity by the heating spot having a dimension different from the initial dimension and created by the heater with a power different from the initial power, the heating spot moving along the surface of the sample in a straight line in the opposite direction with a constant velocity different from the initial velocity and preventing overheating and/or destruction of the sample of the heterogeneous material,
registering a temperature of the heated surface of the sample of the heterogeneous material and of the heated samples with the known thermal conductivity and thermal diffusivity behind the heating spot along the trajectory of the heating spot by a third sensor moving along the trajectory of the heating spot in the opposite direction with a velocity equal to the velocity of the heating spot, a distance between the third temperature sensor and the heating spot providing measurements for a layer of the sample of the heterogeneous material with depth and width different from the initial depth and width,
registering initial temperatures of the surface of the sample of heterogeneous material and of the samples with the known thermal conductivity and thermal diffusivity along the trajectory of the heating spot in front of the heating spot at the first distance by the first temperature sensor moving along the trajectory of the heating spot in the opposite direction with a velocity equal to the velocity of the heating,
determining distribution of thermal conductivity and thermal diffusivity of the sample of the heterogeneous material along the trajectory of the heating spot in the layers of the sample with different depth and width studied during the forward and opposite moving based on results of temperature registrations by the temperature sensors moved in the forward and the opposite directions and on thermal conductivity and thermal diffusivity of the samples with the known thermal conductivity and thermal diffusivity.

2. The method of claim 1 wherein the distance between the third temperature sensor and the heating spot simultaneously provides a specified accuracy of the measurements and a highest spatial resolution capacity when registering the sample heterogeneity along the line of thermal conductivity profile measurements.

3. The method of claim 1 wherein the distance between the third temperature sensor and the heating spot is specified in advance, before heating and measurements.

4. The method of claim 1 wherein the distance between the third temperature sensor and the heating spot is specified before heating and measurements carried out during moving in the opposite direction.

5. The method of claim 1 wherein the surface of the sample is heated by the heating spot moving along the surface of the sample of the heterogeneous material and the samples with the known thermal conductivity and thermal diffusivity, in a straight line in the opposite direction along the line parallel to the trajectory of the heating spot.

* * * * *